(12) United States Patent
Thundat et al.

(10) Patent No.: US 6,763,705 B1
(45) Date of Patent: Jul. 20, 2004

(54) HIGH THROUGHPUT MICROCANTILEVER DETECTOR

(75) Inventors: Thomas G. Thundat, Knoxville, TN (US); Thomas L. Ferrell, Knoxville, TN (US); Karolyn M. Hansen, Knoxville, TN (US); Fang Tian, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 10/462,249

(22) Filed: Jun. 16, 2003

(51) Int. Cl.[7] ............................................. G01N 27/00
(52) U.S. Cl. ..................................... 73/64.53; 422/68.1
(58) Field of Search ........................... 73/21.01, 24.06, 73/61.45, 61.75, 61.79, 64.53, 64.54, 866; 422/68.1, 82.01

(56) References Cited

U.S. PATENT DOCUMENTS

| | | |
|---|---|---|
| 5,445,008 A | 8/1995 | Wachter et al. |
| 5,503,010 A * | 4/1996 | Yamanaka .................... 73/105 |
| 5,719,324 A | 2/1998 | Thundat et al. |
| 5,835,477 A | 11/1998 | Binnig et al. |
| 6,016,686 A | 1/2000 | Thundat |
| 6,289,717 B1 | 9/2001 | Thundat et al. |

OTHER PUBLICATIONS

Fritz, J., Translating Biomolecular Recognition into Nanomechanics, Science Apr. 14, 2000, pp. 316–318, vol. 288.
Hansen, K., Cantilever–Based Optical Deflection Assay for Discrimination of DNA Single–Nucleotide Mismathces, Analytical Chemistry, Apr. 1, 2001, 1567–1571, vol. 73.
Tortonese, R., Atomic Resolution with an atomic force microscope using piezoresistive detection, Appl. Phys. Lett. Feb. 22, 1993, pp. 834–836, vol. 62.
Minne, S., Parallel atomic force microscopy using cantilevers with integrated piezoresistive sensors and integrated piezoelectric actuators, Appl. Phys. Lett., Dec. 25, 1995, pp. 3918–3920, 67(26).

* cited by examiner

*Primary Examiner*—Robert Raevis
(74) *Attorney, Agent, or Firm*—Shelley L. Stafford

(57) ABSTRACT

In an improved uncoated microcantilever detector, the sample sites are placed on a separate semi-conducting substrate and the microcantilever element detects and measures the changes before and after a chemical interaction or hybridization of the sites by sensing differences of phase angle between an alternating voltage applied to the microcantilever element and vibration of the microcantilever element. In another embodiment of the invention, multiple sample sites are on a sample array wherein an array of microcantilever elements detect and measure the change before and after chemical interactions or hybridizations of the sample sites.

41 Claims, 10 Drawing Sheets

HIGH THROUGHPUT MICROCANTILEVER DETECTOR

CROSS-REFERENCE TO RELATED APPLICATIONS

U.S. Pat. No. 5,445,008 issued Aug. 29, 1995 to Wachter and Thundat describes a microcantilever sensor based on variation in adsorbed mass, the entire disclosure of which is hereby incorporated by reference, and U.S. Pat. No. 5,719,324 issued on Feb. 17, 1998 by Thundat and Wachter describes a microcantilever sensor based on variation in surface stress, the entire disclosure of which is hereby incorporated by reference.

The United States Government has rights in this invention pursuant to contract no. DE-AC0500OR22725between the United States Department of Energy and UT-Battelle, LLC.

FIELD OF THE INVENTION

The present invention relates to an improved microcantilever detector and a microcantilever array, and more particularly to an uncoated microcantilever detector used in high throughput detection applications, particularly for detecting hybridization interactions as well as other chemical and biochemical interactions.

BACKGROUND OF THE INVENTION

Microcantilevers have been demonstrated to be extremely sensitive chemical and biological sensors. The microcantilever resonance frequency changes due to adsorption-induced mass loading. The cantilever also undergoes bending due to adsorption-induced surface stress variation if the adsorption is confined to a single surface. The superior sensitivity of the microcantilever is due to its extremely small mass. In U.S. Pat. No. 5,445,008, Wachter and Thundat describe a microcantilever sensor based on variations in adsorbed mass.

One important disadvantage of a microcantilever sensor is the inability to distinguish between different chemical species. This disadvantage also exists on other mass sensors such as the quartz crystal microbalance (QCM), surface acoustic wave device (SAW), plate wave resonator, and the Lamb and Love wave sensor.

To overcome the disadvantage of lack of chemical selectivity, cantilevers are often-coated with a chemically selective layer. However, this chemically selective layer does not provide absolute chemical selectivity except in the case of biosensors based on antibody-antigen interaction or DNA hybridization. This disadvantage can be overcome by using pattern recognition and orthogonal arrays where each element in the array is coated with a specific chemically selective coating that provides a unique signal.

One important advantage of microcantilever sensors lies in the ability to be arranged into an array for detection of a large number of analytes using a single chip since microcantilevers are very small and a large number of sensor elements can be micro-machined on a single chip. However, one of the main disadvantages of the microcantilever technology is that in an array format, every element in the array must be modified by a different chemical species. This is a very challenging task since the surface area of the cantilever is very small. In addition, when a large number of analytes are present, it is necessary to use pattern recognition techniques for identifying analytes.

However, when only "yes" or "no" answers are involved, using a microcantilever as a chemically selective analytical tool is redundant and costly. First and foremost, it is extremely difficult and time consuming to modify every single microcantilever in the array with a discrete chemically selective layer. Secondly, the quality of the deposited film cannot be guaranteed. Thirdly, signal processing from a large number of sensor elements is extremely expensive and involves development of algorithms that can handle multiple input including reference signals. For example, the cantilever response (bending and frequency change) varies with physical parameters such as pressure, temperature, flow rate, pH, presence of ions in the solutions, and other parameters. Relative humidity plays a major role when microcantilevers are used in air.

In the past, the use of the microcantilever detector concept, especially in array applications, has been costly and cumbersome. In recent years, great advances have been made in array technology. For example, many commercially available array chips such as the Affimetrix chip exist. In conventional chips, such as DNA chips, areas as small as 5 $\mu$m by 5 $\mu$m are modified with definite sequences of single-stranded DNA. These areas form a well-defined array. When a target sequence is introduced, they hybridize with a complimentary sequence in a particular area. In general, targets are tagged with a fluorescent marker, which when exposed to an appropriate wavelength, produces a particular color. This technology, though widely used, suffers from lack of simplicity in reading due to the multiple steps involved.

In response to the need for further research, improved microcantilever apparatuses, microcantilever array and methods of use have been developed. The apparatuses, array and methods disclosed herein are extremely useful for high throughput operations.

OBJECTS OF THE INVENTION

Accordingly, objects of the present invention include apparatus and methods for an improved uncoated microcantilever detector, particularly, an uncoated microcantilever detector and microcantilever detector array wherein the sample sites are placed on a separate semi-conducting or conducting substrate and the microcantilever(s) measures the changes before and after chemical/biochemical interaction or hybridization of the sites. Further and other objects of the present invention will become apparent from the description contained herein.

SUMMARY OF THE INVENTION

In accordance with one aspect of the present invention, the foregoing and other objects are achieved by an uncoated microcantilever detector apparatus which comprises at least a first microcantilever element, the microcantilever element being uncoated and comprising a material selected from the group consisting of electrically conductive materials and electrically semi-conductive materials; a substrate disposed relative to the first microcantilever element with a known, controlled gap therebetween, the substrate comprising a material selected from the group consisting of electrically conductive materials and electrically semi-conductive materials, the substrate further comprising means for attaching at least one sample upon the substrate proximate to the microcantilever element; a vibration detection means for detecting vibration of the first microcantilever element and providing vibration data; alternating voltage means disposed and connected for imposing an alternating voltage electrical signal to the substrate with respect to the first microcantilever element to induce vibration in the first microcantilever element; instrumentation means disposed and in communication with the first microcantilever element for receiving the vibration data and to determine frequency and amplitude of vibration of the first microcantilever element and for sensing and quantifying the alternating voltage electrical signal applied to the substrate with respect to the first microcantilever element, and further for detecting and quantifying differences in phase angle between the signal applied by the alternating voltage means and the signal generated by the vibration detection means; and the first microcantilever element, the substrate, the vibration detection means, the alternating voltage means, and the instrumentation means being configured to permit a test fluid to pass between the first microcantilever element and the substrate so that a chemical interaction may occur between a component of the test fluid and a component of the sample.

In accordance with a second aspect of the present invention, a method for detecting a component-capable of chemical interaction or hybridization in a fluid test sample comprises the steps of: providing an uncoated microcantilever detector apparatus which comprises at least one microcantilever element, the microcantilever element being uncoated and comprising a material selected from the group consisting of electrically conductive materials and electrically semi-conductive materials, also comprising a substrate positioned adjacent the microcantilever element and disposed relative to the microcantilever element with a known, controlled gap therebetween, the substrate comprising a material selected from the group consisting of electrically conductive materials and electrically semi-conductive materials, the substrate further comprising means for attaching at least one sample upon the substrate proximate to the microcantilever element, further comprising a vibration detection means for detecting vibration of the microcantilever element and providing vibration data, alternating voltage means disposed and connected for imposing an alternating voltage electrical signal to the substrate with respect to the microcantilever element to induce vibration in the microcantilever element, an instrumentation means disposed and connected for receiving vibration data and to determine frequency and amplitude of vibration of the microcantilever element and for sensing and quantifying the alternating voltage electrical signal applied to the substrate with respect to the microcantilever element, and also for detecting and quantifying differences in phase angle between the signal applied by the alternating voltage means and the signal generated by the vibration detection means, the microcantilever element, the substrate, the vibration detection means, the alternating voltage means, and the instrumentation means being configured to permit a test fluid to pass between the microcantilever element and the substrate so that a chemical reaction or hybridization may occur between a component of the test fluid and a component of the sample; causing the test fluid to pass between the microcantilever element and the substrate to allow chemical interaction or hybridization to occur; and determining the frequency and amplitude of vibration of the microcantilever element and quantifying differences in phase angle between the alternating voltage electrical signal applied by the alternating voltage means and signal generated by the vibration detection means to determine whether a chemical interaction or hybridization occurred and to determine the extent of chemical interaction or hybridization which may have occurred between a component of the test fluid and a component of the sample.

For a better understanding of the present invention, together with other and firther objects, advantages and capabilities thereof, reference is made to the following disclosure and appended claims in connection with the above-described drawings.

DETAILED DESCRIPTION OF THE INVENTION

Figure 1A:
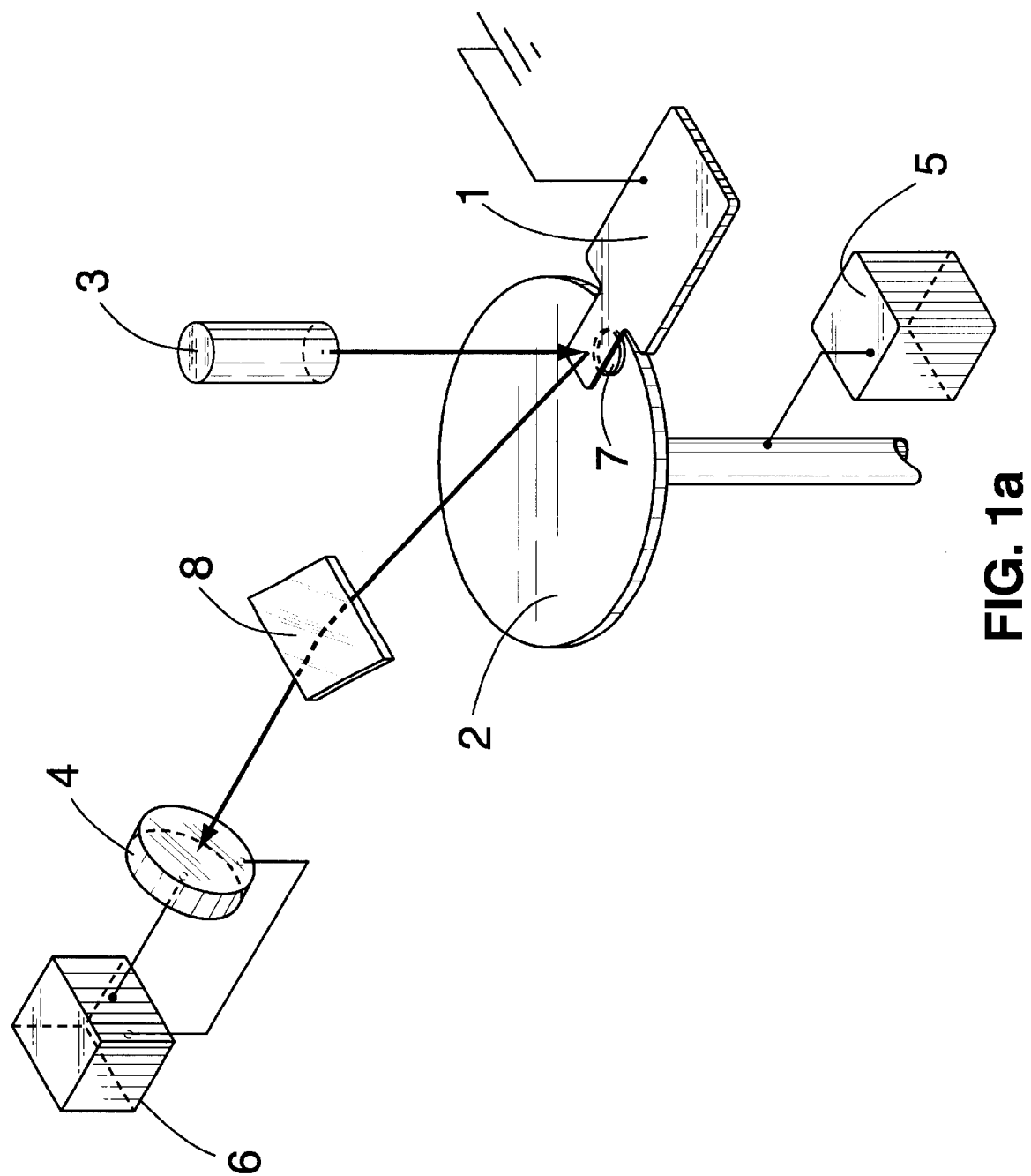
FIG. 1a is a schematic representation of an apparatus comprising a single microcantilever detector wherein the sample analyte is at a sample site on a separate semiconducting or conducting substrate and the microcantilever measures the changes before and after chemical interaction or hybridization of the sites using optical detection means.
Figure 1B:
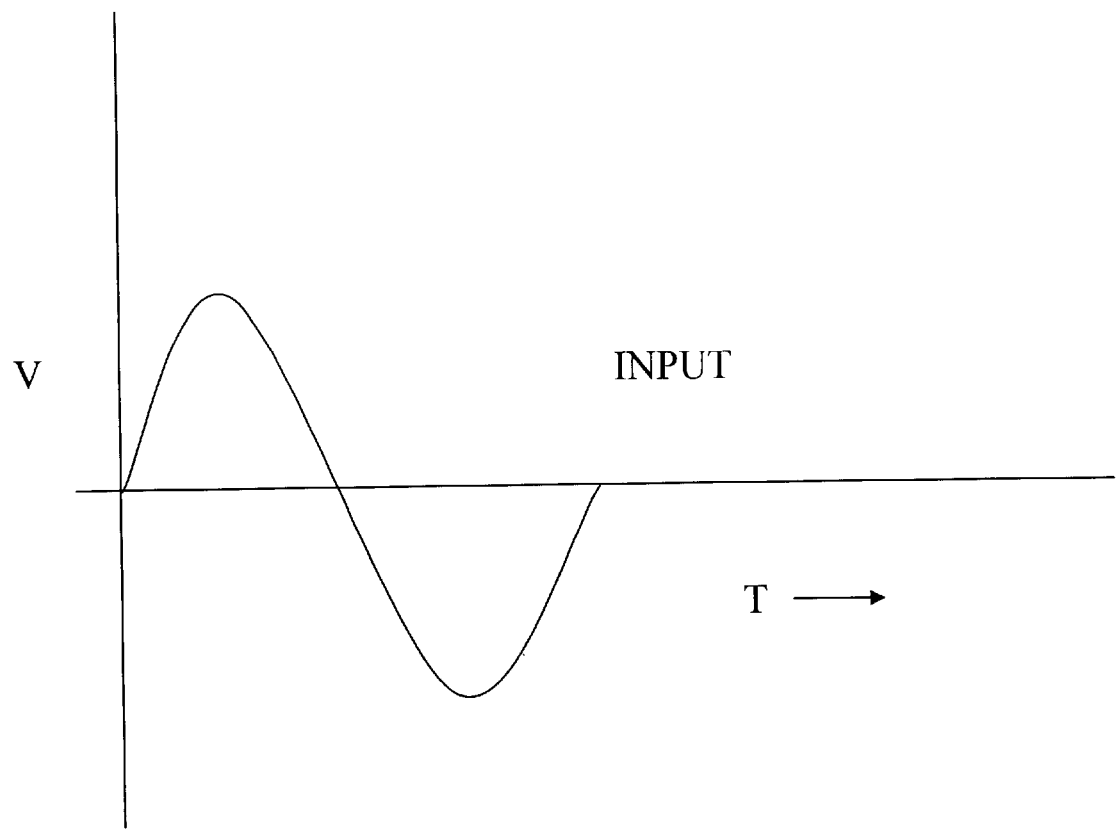
FIG. 1b is a voltage-time curve of the alternating voltage signal applied to the substrate.
Figure 1C:
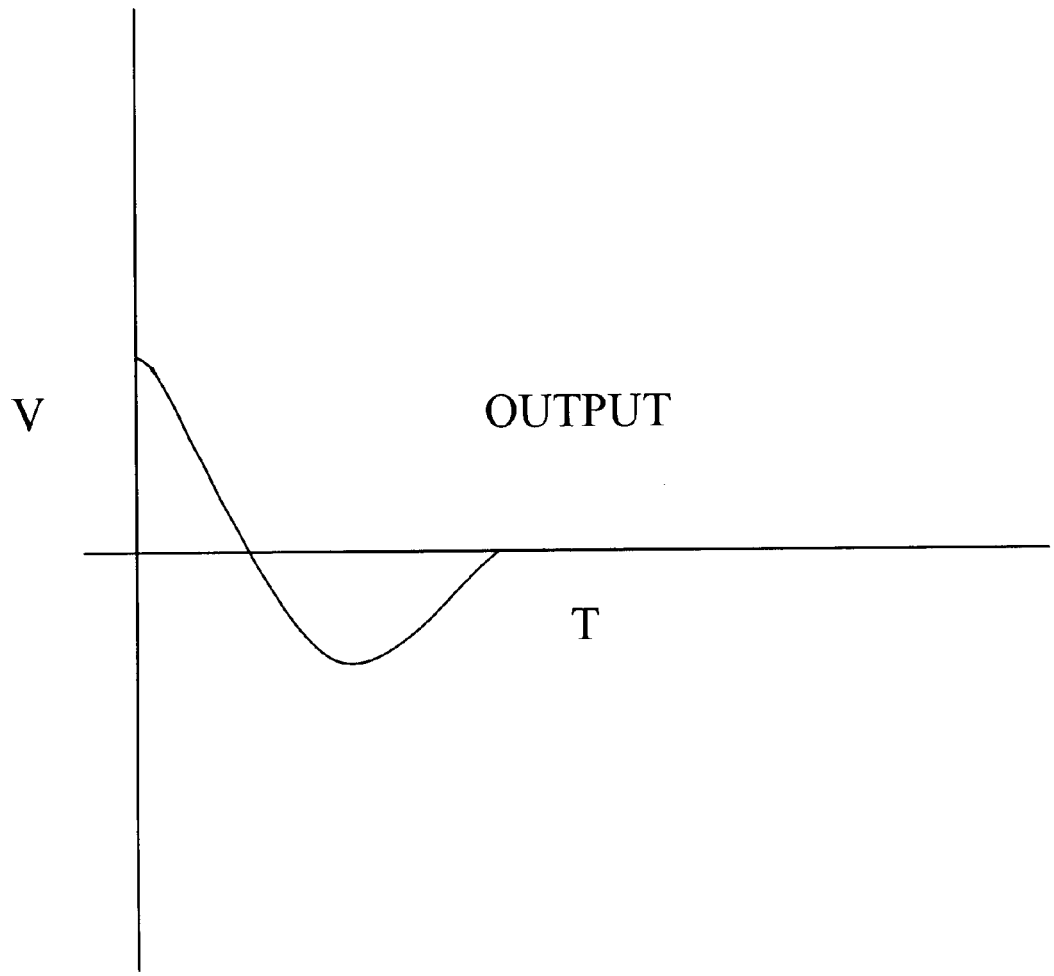
FIG. 1c shows a phase difference or the response of the microcantilever as a result of being driven by the applied signal in FIG. 1b.

In the present invention, the conventional array and the microcantilever sensor are combined in a way to provide simplicity of both apparatus and method. First, arrays are made in the same fashion as those used in conventional techniques. However, there is no need for tagging the targets with fluorescent dyes. The present invention comprises an uncoated microcantilever placed at a definite, controlled distance above the array or above the substrate having sample sites wherein the uncoated microcantilever operates as a sensor, in a fashion similar to that of a magnetic read head in a computer hard drive. Binnig et al., describe a two-dimensional array of cantilevers for direct writing of features on a substrate that is placed in close proximity of the cantilever array (incorporated herein by reference). The motion or bending of the microcantilever may be monitored using a laser diode focused at the apex of the microcantilever as the laser is reflected into a position-sensitive photodetector. Alternatively, the motion of the microcantilever can also be measured using piezoresistance or piezoelectric means. Tortonese et al., for example, demonstrate detection of cantilever motion using piezoresistive method whereby bending of the cantilever results in change of cantilever resistance, incorporated herein by reference. In addition, Minne et al., demonstrate cantilever motion detection using piezoelectric method whereby the cantilever coated with a piezoelectric material results in a charging current due to piezoelectric nature of the coating material (incorporated herein by reference). In the embodiment as shown in FIG. 1a, a single microcantilever 1 having a light-reflecting surface is positioned adjacent to and above a substrate 2 wherein there exists a definite, controlled gap therebetween. FIG. 1a shows the microcantilever 1 being grounded. The substrate 2 has a sample site 7 on its surface wherein the sample is attached thereon the sample site. The substrate 2 comprises a material that is electrically conductive or electrically semi-conductive. FIG. 1a further shows an alternating voltage means 5 that can be used to apply an alternating voltage electrical signal to the substrate 2 which thereby imposes the alternating voltage electrical signal between the substrate 2 and the microcantilever 1 which sets the microcantilever 1 into oscillation (Sarid, incorporated herein by reference, describes exciting cantilevers placed in close proximity of a substrate by applying alternating voltage on the substrate. By adjusting the frequency of the alternating voltage applied to the substrate, it is possible to excite the cantilever into resonance.). A laser light source 3 is focused onto a surface of the microcantilevey 1 so that a reflection of the laser light beam impinges upon a position-sensitive photodetector 4. One or more mirrors or prisms 8 may be utilized to project the laser light beam upon the position-sensitive photodetector 4. When the applied alternating voltage frequency matches with the resonance frequency of the microcantilever, the oscillation amplitudes increase to a maximum corresponding resonance. The motion of the microcantilever is monitored using the signal from the position-sensitive detector 4. There exists a phase difference between the applied alternating voltage frequency and the alternating voltage electrical signal obtained from the position-sensitive photodetectbr 4. This phase difference is duet to the presence of hybridized material or other material that has chemically interacted wherein a sample component attached to the substrate has bonded with a component of a test fluid that is present in the gap between the microcantilever 1 and the substrate 2. Therefore, there will be a marked difference in the phase shift before and after hybridization or other chemical/biochemical interaction. Thus, real-time hybridization or chemical/biochemical interaction can be monitored using the present invention. Chemical/biocheniical interactions include DNA hybridization, chemical and biochemical interactions such as protein-protein interaction, ligand-protein interaction, antibody-antigen interaction, etc. Instrumentation apparatus 6 detects and quantifies the vibrational frequency and amplitude of the microcantilever 1, then compares and quantifies differences in phase angle between the applied alternating voltage electrical signal and the signal generated by the position-sensitive photodetector 4. FIG. 1b shows a voltage-time curve of the applied alternating voltage signal applied to the substrate 2. FIG. 1c is the response of the microcantilever as a result of being driven by the applied alternating voltage signal applied to the substrate, shown in FIG. 1b. FIG. 1c shows the phase difference.

Thundat et al. describe biological applications of a microcantilever sensor in U.S. Pat. No. 6,016,686 issued on Jan. 25, 2000, incorporated herein by reference. Fritz et al. describe a one dimensional cantilever array for DNA hybridization detection, incorporated herein by reference. Hansen et al. describe detection of single nucleotide polymorphism using cantilever sensors, incorporated herein by reference. In all these cases, the cantilever or cantilever array was modified by immobilizing biologically specific molecules on one side of a cantilever.

Figure 2:
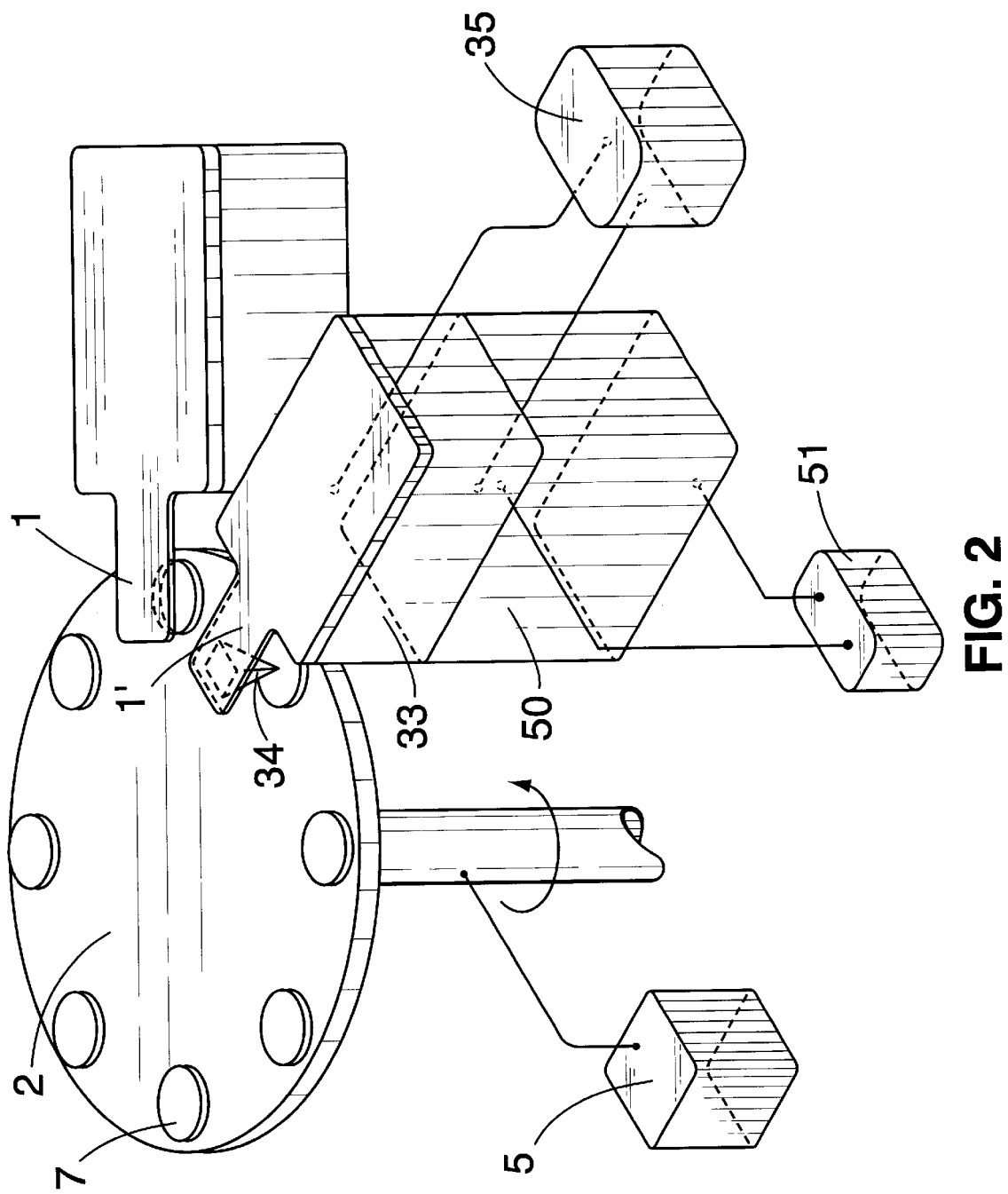
FIG. 2 is a schematic showing a circular disc substrate having a multiplicity of sample sites and showing two uncoated microcantilevers wherein one microcantilever operates as a sensor for measuring changes before and after chemical or biochemical interaction or hybridization of the sample analyte at the sample sites and wherein the second uncoated microcantilever having piezoelectric means operates as a position-monitoring microcantilever for measuring the separation distance between the second microcantilever and the sample.

In the embodiment shown in FIG. 2, the substrate 2 has numerous sample sites 7; and as in FIG. 1a, an alternating voltage electrical signal is applied to the substrate 2 imposing the alternating voltage electrical signal between the substrate 2 and the microcantilever 1, which sets the microcantilever 1 into oscillation. The substrate can be moved relative to the microcantilever 1 to detect the presence of a sample within a sample site 7. The distance between the microcantilever 1 and the substrate 2 is adjusted in such a way that the electric field between the microcantilever 1 and the substrate 2 is high enough to affect the motion of the microcantilever 1. As the alternating voltage electrical signal is applied to the substrate 2, the microcantilever 1 undergoes vibrational oscillation. The microcantilever 1 or microcantilever array goes into vibrational mode because of the electrostatic interaction between the microcantilever 1 and the field emanating from the substrate 2. When the applied frequency matches with the resonant frequency of the microcantilever 1, the oscillation amplitude increases to a maximum corresponding resonance. The bending or motion of the microcantilever 1 may be monitored using, for example, the laser deflection technique. There exists a phase angle difference between the applied alternating voltage frequency and the alternating signal obtained from the photodetector 4. This phase angle difference is due to material present in the gap between the microcantilever 1 and the substrate 2. Therefore, there will be a measurable difference in the phase shift before and after hybridization.

As one embodiment is shown in FIG. 2, the substrate 2 may be shaped such that it can be rotated with respect to its axis or orthagonally translated using a motor arrangement, such as a stepper motor. The shape may be any that permits a multiplicity of sample areas or sites 7, such as a disc, drum, or other arrangement. The arrangement is electrically configured in such a way that the moving substrate 2 is in electrical contact with an alternating voltage means, which is an alternating voltage source of variable frequency 5. The frequency of the alternating voltage means 5 is varied such that it matches with the resonance frequency of the microcantilever 1. The alternating voltage means 5 may include a d.c. offset voltage. The resonance condition can be monitored using the vibrational amplitude of the microcantilever 1. At resonance, the amplitude reaches a maximum. The substrate 2 is moved in such a way that different modified sample areas and unmodified sample areas come under the sensing microcantilever 1 in a sequential manner, and th substrate 2 is held in position for a time long enough to determine the phase and amplitude of the microcantilever 1. In some embodiments, the sensing microcantilever 1 can also be translated to sense signals from additional regions that have been modified in similar or in different ways.

In addition to phase angle, the amplitude of oscillation of the microcantilever 1 changes when chemically reacted regions or hybridized regions exist under the microcantilever 1 and the microcantilever 1 is set into resonance by applying the alternating voltage bias to the substrate 2.

In another embodiment, the microcantilever response detection system is a piezoresistive or piezoelectric means. It is possible to use a one-dimensional or two-dimensional array of microcantilevers for simultaneous detection of chemical and biochemical interactions.

In yet another embodiment, the vibration response of a microcantilever is monitored at the harmonics of the frequency applied to the substrate.

In all these cases, the microcantilever 1 is electrically grounded. The magnitude of the amplitude of vibration of the microcantilever 1 depends on the distance between the substrate 2 and the microcantilever 1. Therefore, when amplitude is used as a chemical interaction or hybridization detection signal, a method for measuring the distance between the microcantilever 1 and the substrate 2 is necessary. In this embodiment, using amplitude as a detection signal for a chemical interaction, as shown in FIG. 2, this measurement is accomplished using a proximity sensing means comprising a second microcantilever 1' brought into close proximity to the substrate 2 by a proximity controlling means. The proximity sensing means is connected to the second microcantilever 1'. In this embodiment, the microcantilever used for sensing is called the sensing microcantilever 1 and the microcantilever 1 used for monitoring the distance is tile position-monitoring microcantilever. The position-monitoring microcantilever 1' keeps the distance between the microcantilever 1 and the substrate 2 containing the samples, constant. Initially the microcantilevers 1 are 1' are in one plane. The microcantilever 1' is vibrated into resonance by a small piezoelectric element 33, vibrated by applying voltage means 35. This position-monitoring microcantilever 1' has a sharp tip or a bump 34 at its free end. This tip 34 is normal to its bending axis such that when the distance between the microcantilever 1' and the substrate 2 is decreased, the tip 34 comes in contact or near contact with the substrate 2 before the microcantilever 1'. This avoids sticking the microcantilever 1 to the substrate 2 in case the device is operated in ambient air. The position-monitoring microcantilever 1' is brought into contact with the substrate 2 using a proximity controlling means. The proximity controlling means, connected to the position-monitoring microcantilever 1', comprises a piezoelectric transducer 50 whose translation is controlled by voltage applied by voltage means 51. The proximity controlling means further comprises the piezoelectric element 33, which is fixedly attached to the position-monitoring microcantilever 1'. The piezoelectric element 33 is configured to vibrate the microcantilever 1' into resonance. When this microcantilever 1' is brought in close proximity of the surface of the substrate 2 using the piezoelectric transducer 50, the amplitude of the microcantilever vibration changes and this change is sensed using either optical means, piezoresistive means or using piezoelectric means (not shown in FIG. 2). The amplitude of vibration of the microcantilever 1 is a measure of proximity between the microcantilever 1' and the substrate 2. Furthermore, the vertical displacement of the microcantilever 1' is a function of the voltage applied to the piezoelectric transducer 50. It is also possible to use microcantilever 1' as the sensing microcantilever. In this case, the sensing microcantilever and position-monitoring microcantilever are the same.

In other embodiments, other methods, all well known to the skilled artisan, including a non-vibrating microcantilever (without the use of a piezoelectric element 33 or voltage means 35) can be used to monitor position of the microcantilever to the surface of the substrate. When such a non-vibrating microcantilever comes in contact with the surface, the microcantilever bending changes drastically. In this case, the distance between the position-sensing microcantilever 1' and the substrate 2 is proportional to the bending of the microcantilever 1'.

Figure 3:
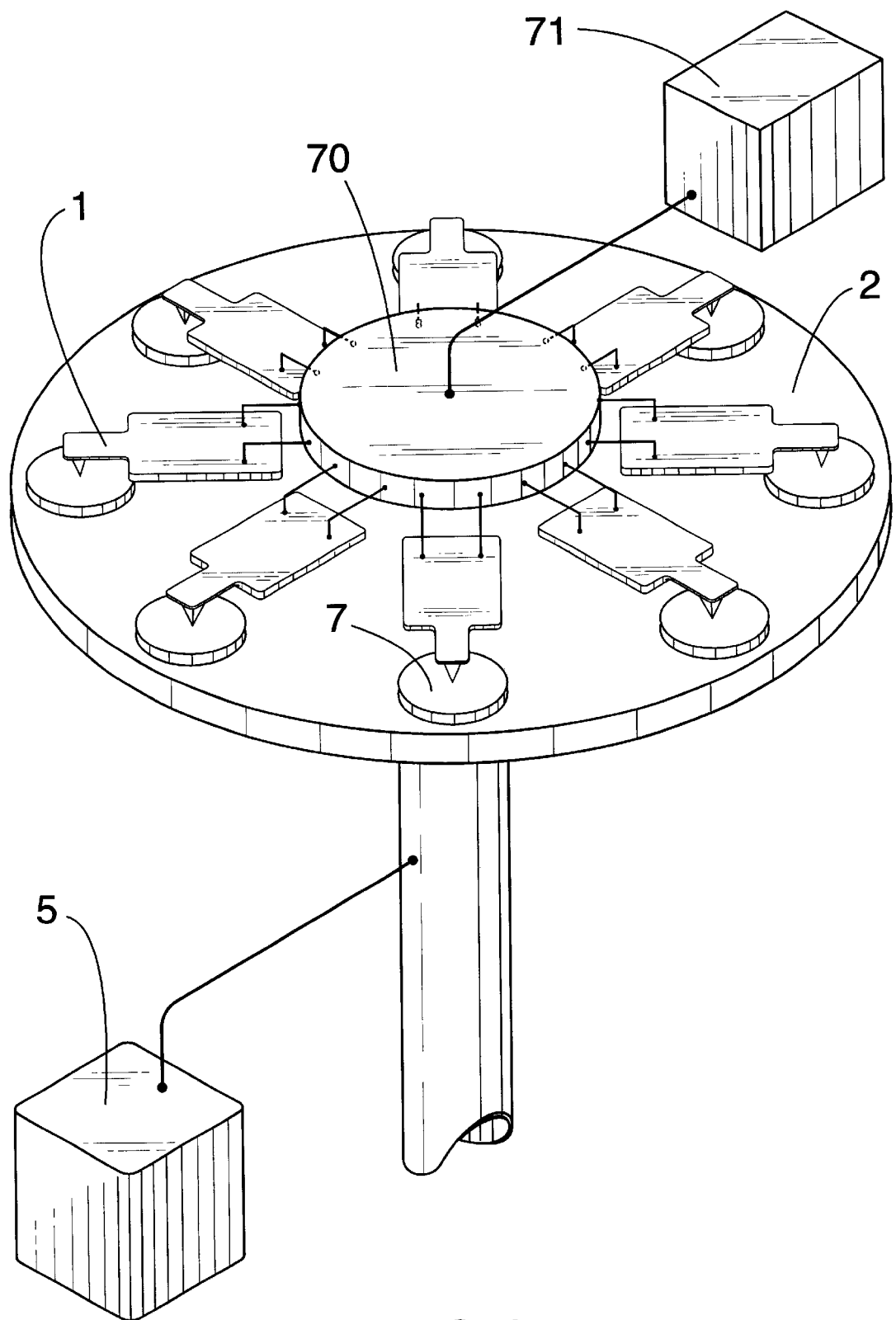
FIG. 3 illustrates a circular disc substrate having a multiplicity of sample sites and an array of multiple microcantilevers arranged above the substrate wherein each microcantilever is above a sample site in the substrate wherein the motion of each microcantilever of the array is independently monitored using piezoresistive or piezoelectric means, the microcantilevers operate as sensing microcantilevers and/or as position-monitoring microcantilevers for measuring the distance between the microcantilevers and the substrate.

In yet another embodiment shown in FIG. 3, multiple samples are spotted on sample sites 7, on substrate 2 and an array 70 of multiple microcantilevers are arranged above the substrate 2 wherein each microcantilever 1 of the array 70 is located above the sample sites 7 on the substrate 2 wherein there exists a definite, controlled gap between each microcantilever 1 and the respective sample site 7. In FIG. 3, the microcantilevers 1 are read optically; however, the array 70 may also comprise microcantilevers having piezoelectric means such as microcantilever 80 as shown in FIG. 4 that have piezoelectric readout, or microcantilevers having piezoresistive means such as microcantilever 31 as shown in FIG. 5 that have piezoresistive readout.

In the case of FIG. 3, the motion of each microcantilever member of the array 70 is independently monitored, for example using piezoresistive or piezoelectric means. All the microcantilever responses are read out simultaneously using a multiplexer, located within the array 70, and a display unit 71. The signal transduction mechanism can be piezoelectric or piezoresistive.

In a microcantilever array, all the microcantilevers have the same readout technique. Optical readout is used for single cantilever or a linear array with limited number of microcantilevers. Piezoresistive or piezoelectric means is used for two-dimensional arrays, such as in FIG. 3.

Figure 4:
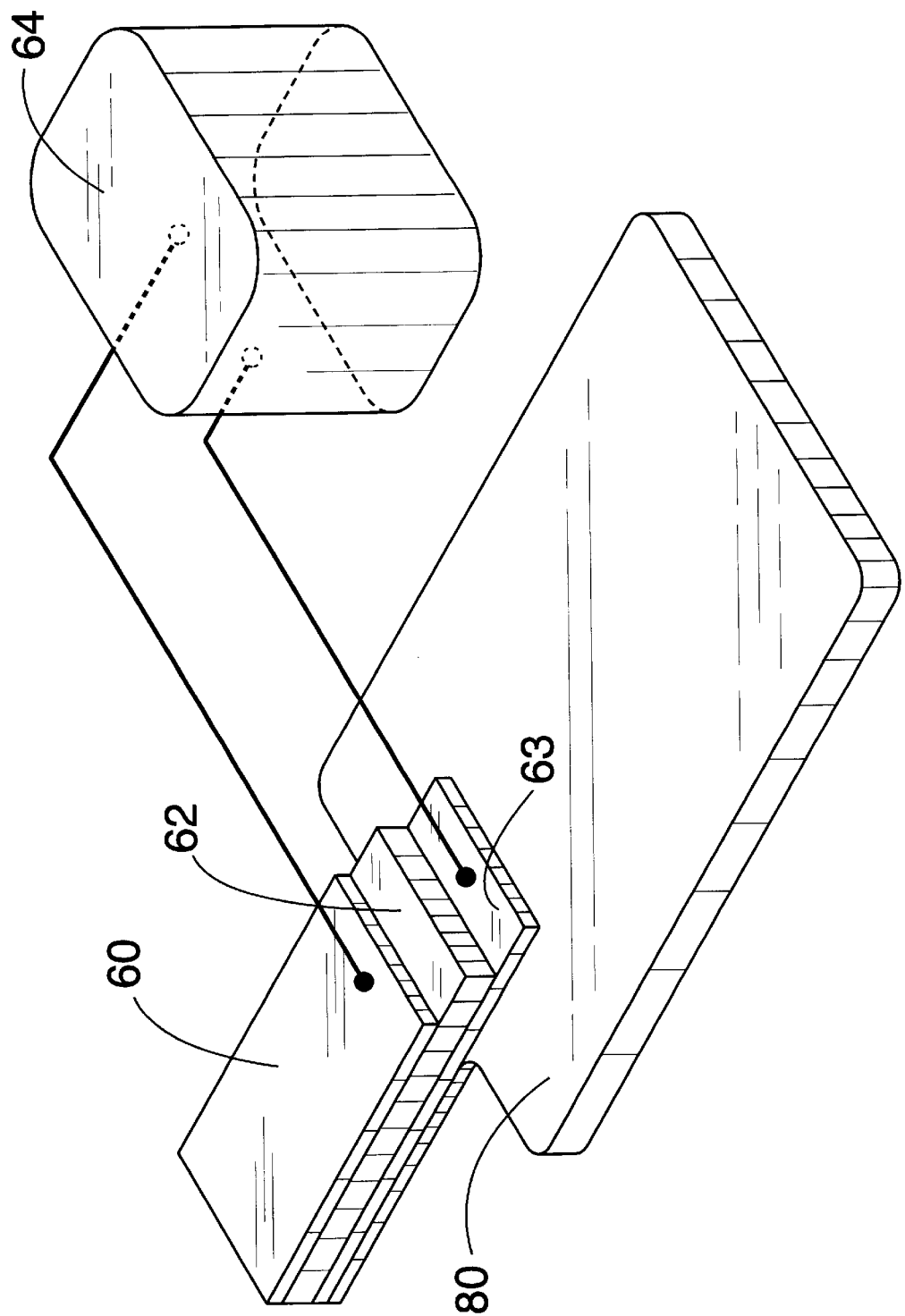
FIG. 4 is a schematic showing a microcantilever sensing element having a piezoelectric means wherein the piezoelectric element such as zinc oxide is sandwiched between two electrodes.
Figure 5:
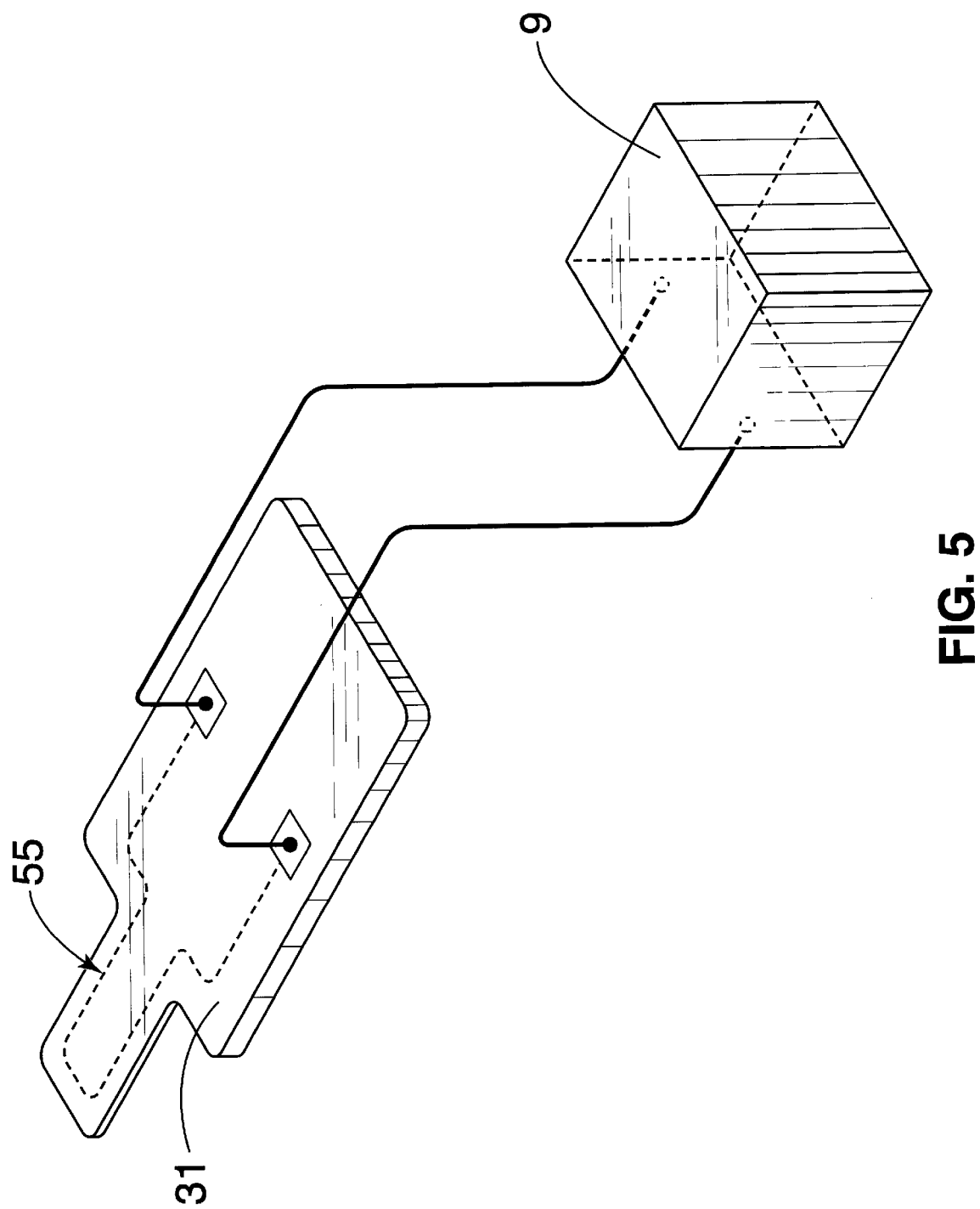
FIG. 5 shows a sensing microcantilever having a piezoresistive means wherein a thin layer of boron channel is embedded in the microcantilever whereby when the microcantilever bends, the resistance of the embedded channel changes and is monitored.

FIG. 4 shows a microcantilever sensing element 80 wherein the signal transduction means is a piezoelectric means wherein a piezoelectric element such as zinc oxide (ZnO) 62 is sandwiched between electrode 60 and electrode 63. Vibration of microcantilever 80 produces electrical charges in the piezoelectric element 62, which is then measured by charge amplifier 64.

In another embodiment, vibration detection means may be provided by piezoresistive properties of the sensing microcantilever 31 (shown in FIG. 5). In this embodiment, a Wheatstone bridge or other electrical circuitry 9 (FIG. 5), known to the skilled artisan, is utilized to provide vibration data for the microcantilever 31. The sample being analyzed is attached to sample site 7 on the substrate 2 (not shown in FIG. 5, see FIG. 1), proximate the microcantilever 31, and separated from the microcantilever 31 by a definite, controlled gap. In FIG. 1, microcantilever 1 can be replaced by the apparatus of FIG. 5. The microcantilever 31 is set into oscillation by the alternating voltage electrical signal applied to the substrate by alternating voltage means 5. This requires that the substrate 2 and microcantilever 31 or microcantilever array be made from a conducting or semi-conducting material.

FIG. 5 shows a sensing microcantilever 31 wherein the signal transduction means is a piezoresistive means, wherein a thin layer of boron comprises channel 55 embedded within the microcantilever 31. When the microcantilever 31 bends, the resistance of the embedded boron channel changes and is monitored by the Wheatstone bridge 9.

In a previously mentioned embodiment wherein the substrate 2 is made in the shape of a disc that can be rotated about its axis, such as in FIG. 1a or FIG. 2, selected areas or sites of the substrate 2 near the periphery are modified by affixing or attaching samples to be detected. For example, for detecting hybridization of a certain sequence of DNA, the disc is modified in small spots or sample sites 7 with all possible variation of complementary DNA sequences called DNA probes. When this disc is exposed to a solution of DNA-whose sequence is to be determined (called target DNA), the hybridization happens only when there is a match between probe DNA and target DNA. The hybridization process converts the single stranded DNA into double stranded DNA. Washing the disc using a buffer solution removes all the unhybridized DNA strands. In this case, all the spots or sample sites on the substrate disc will remain unchanged except one where hybridization occurred. All the DNA strands on the hybridized region will be double stranded while the remaining sites will be single stranded probes.

In one example, to prepare the substrate, a thin layer of (40–50 nm) gold is deposited on the conducting or semiconducting substrate. Prior to gold deposition, a thin layer (5 nm) of chromium is deposited as an adhesion layer for gold. Different sequences of single stranded DNA with an end thiol group are deposited on the gold substrate in small spots or sites. Each site will have single stranded DNA of different sequences. However, within each site, the sequence of each DNA molecule is identical to that of the other DNA molecules within that site.

This method can also be used for detecting antigens. In this case, each spot or sample site contains antibodies attached to the substrate by thiol binding or covalent linkage. Exposing the substrate results in antibody-antigen binding. Since the antibody-antigen interaction is very specific, only the spot or sample site with correct antibody will have antigens. This method can be extended for detecting different proteins, enzymes and other organic agents. The method of the present invention detects a component or chemical species capable of chemical interactions including hybridization and other biochemical interactions as previously described. A component is defined as a complementary DNA fragment, antigens, antibodies, proteins, enzymes or other organic agent that may be in the test fluid that is capable of interacting with its complement or match which is affixed or attached to the sample site.

The attachment of proteins and. DNA can also be accomplished using silane covalent immobilization bonding. In this case, no gold layer on the substrate is required.

In all these cases, the substrates are pre-fabricated as needed for detection purposes. These discs can be fabricated and stored until needed. This method and apparatus have been demonstrated to work in a liquid solution. Therefore, real-time hybridization can be monitored using this technique. The substrate may be configured in the form of a disk just as in the case of a drive. The microcantilever can be scanned over the substrate or; the substrate can be scanned or rotated under the microcantilever. The substrate may also be configured in the form of a disc having multiple samples arranged in arc patterns or circular patterns about the axis of rotation of the disc. The disc may be a sample array that does not rotate but remains stationary wherein a single microcantilever that is moveable may be used for detection or a microcantilever array may be used for detection. In the case wherein the substrate is a disc having multiple samples arranged in a pattern about the axis of rotation of the disc, a single microcantilever element may be translated radially with respect to the disc in order to sense samples arranged in multiple patterns on the disc. In addition, the samples may be placed in a linear pattern on a substrate, for instance, a continuous tape monitoring cassette may be used as a substrate.

In a preferred embodiment, the arrays of different sequences may be made on a silicon wafer. They also can be made on a metal or semiconductor surface with a thin or thick layer of insulating material such as glass on top.

It is also possible to enhance the phase difference by optically exciting the hybridized areas with electromagnetic waves. In this case, creation of free radicals in the sample changes the dielectric constant.

Figure 6B:
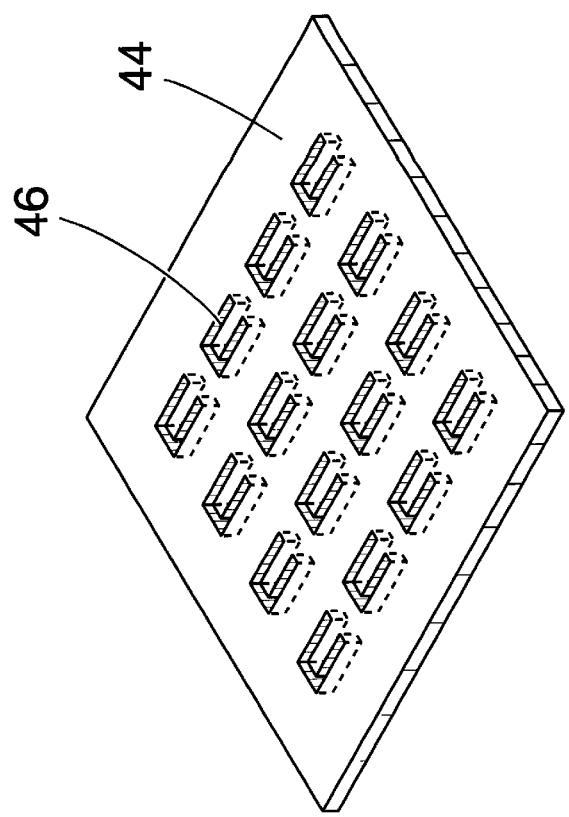
FIG. 6b shows a rectangular array of microcantilevers comprising N×M microcantilevers wherein N is the number of microcantilevers in the x direction of the array and M is the number of microcantilevers in they direction of the array.
Figure 6A:
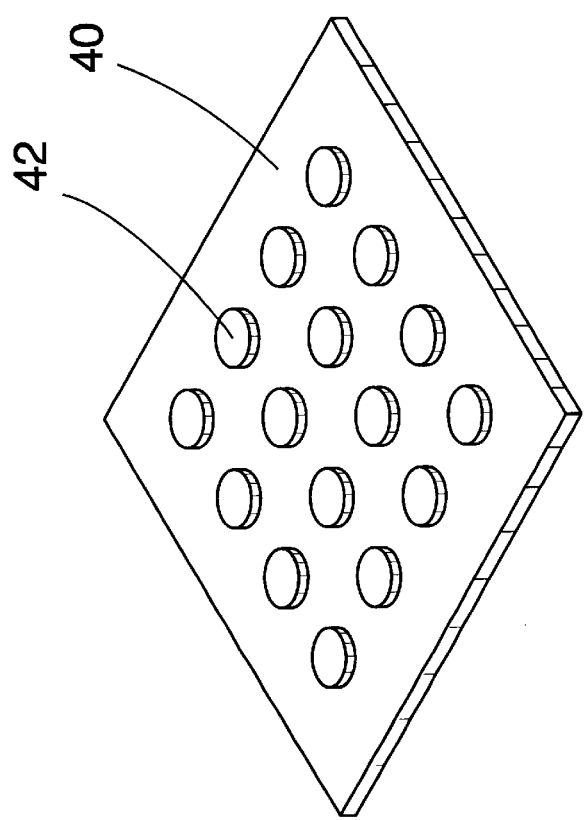
FIG. 6a shows a substrate being a rectangular array of N×M samples thereon the surface of the substrate wherein N is the number of sample sites having samples attached thereto in the x direction of the array and M is the number of sample sites having samples attached thereto in the γ direction of the array.
Figure 6C:
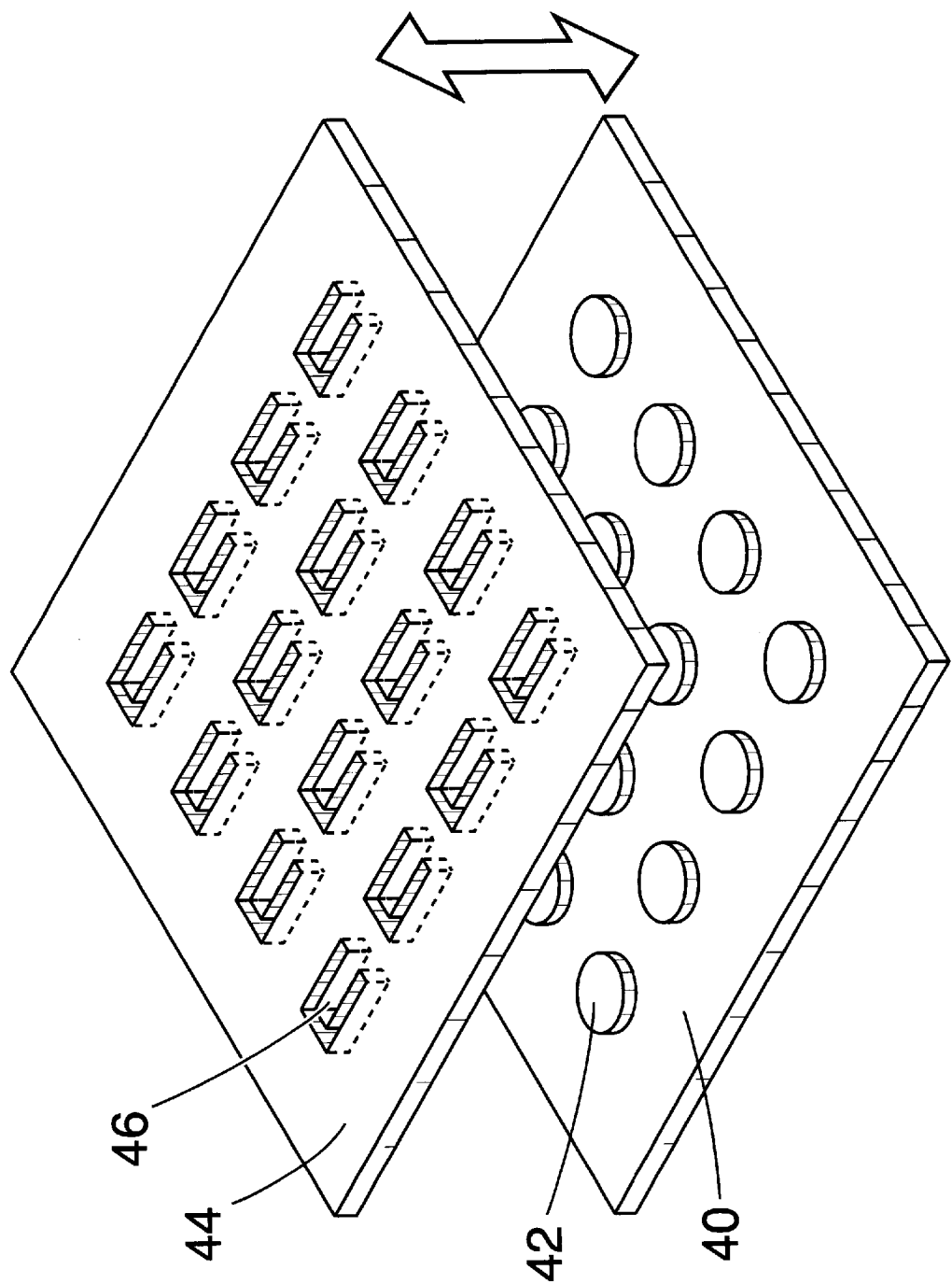
FIG. 6c shows the orientation of the sample array and the microcantilever array wherein the microcantilever array is placed above the substrate array surface in such a way that each microcantilever element is above a sample site and there exists a controlled separation distance in tens of nanometers between the substrate sample array and the microcantilever array.

FIG. 6a shows another embodiment of the present invention, wherein the substrate 40 is a rectangular array having N×M number of sample sites 42 on its surface wherein samples are attached to the sample sites. N is the number of samples in the x direction of the array and M is the number of samples in the y direction of the array. FIG. 6b shows a rectangular array of microcantilevers 44 comprising N×M microcantilevers 46 wherein N is the number of microcantilevers in the x direction of the array and M is the number of microcantilevers in the y direction of the array. Then, FIG. 6c shows the orientation of the sample array and the microcantilever array wherein the microcantilever array 44 is placed above the substrate array surface 40 in such a way that each microcantilever element 46 is above a sample site 42 and there exists a controlled separation distance in tens of nanometers between the substrate sample array 40 and the microcantilever array 44. Some microcantilevers in the array may work as reference microcantilevers for measuring the distance between the microcantilever array and the substrate sample array.

The microcantilever array can have any number of microcantilevers. The microcantilever array can be a one-dimensional array with scanning in the other direction, or a small two-dimensional array that scans in batches. Furthermore, some DNA sample arrays or DNA chips have thousands of sample spots. In an array, all the microcantilevers should have the same readout technique. Optical readout is good for single cantilever or a linear array with limited number of cantilevers. Piezoelectric readout or piezoresistive readout is very useful for two-dimensional microcantilever arrays.

Figure 7:
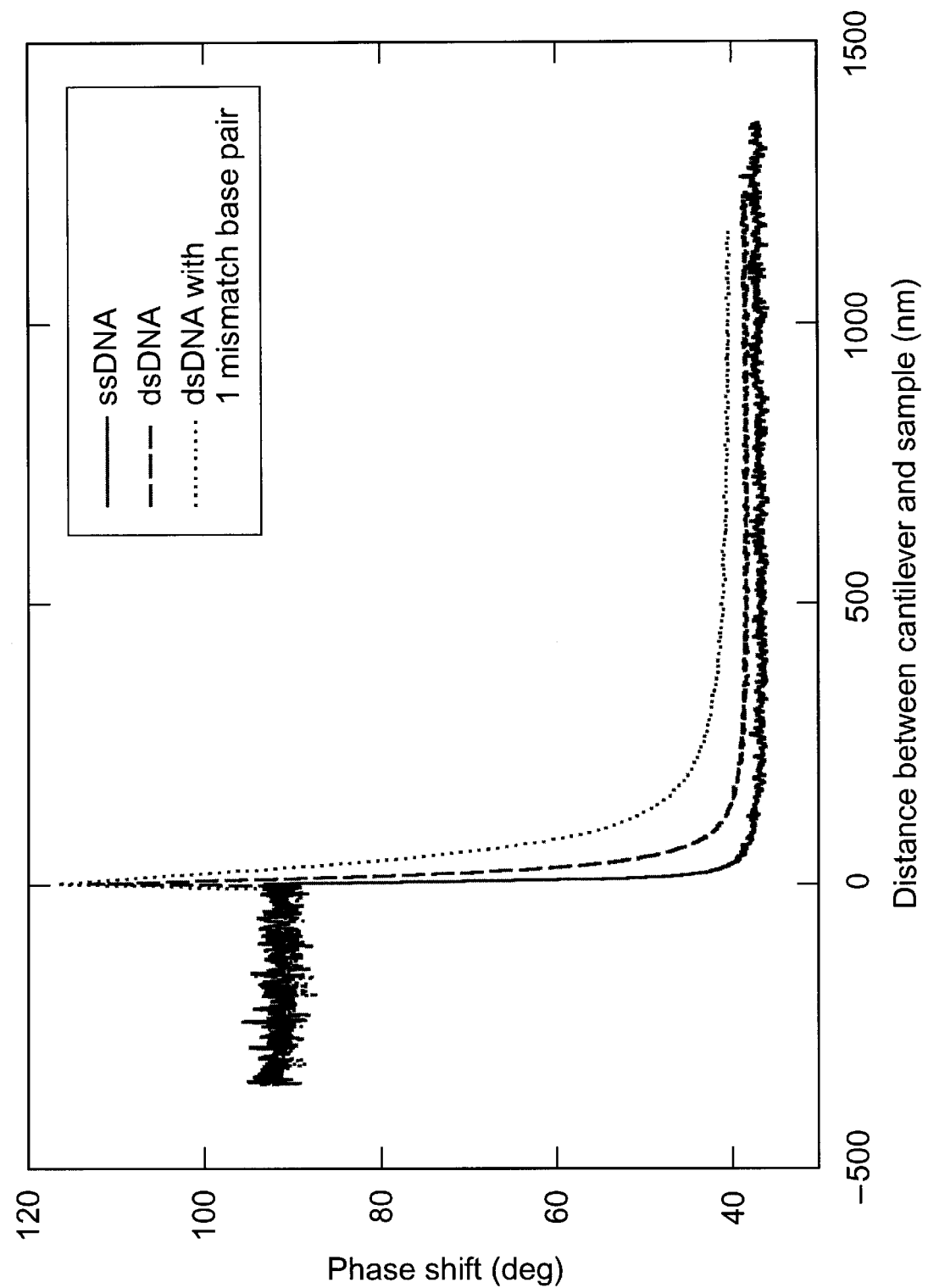
FIG. 7 shows the phase differences as measured by the microcantilever for single stranded DNA, double stranded DNA (after hybridization), and a double stranded DNA with an internal mismatch (after hybridization). This figure shows that the phase difference happens only for small separation distances. The optimum separation distance depends on the frequency of operation.

FIG. 7 shows the phase difference signal from a single stranded DNA (ss DNA), a double stranded DNA (dsDNA), and a double stranded DNA with an internal mismatch (after hybridization). Double stranded DNA is the result of hybridization of complimentary single stranded DNA with first single stranded DNA. This figure shows that the phase difference happens only for small separation distances. The optimum separation distance depends on the frequency of operation.

In the above-described embodiments, the method of operation of these microcantilever detector apparatuses utilizes a means for fluid flow for causing a test fluid to pass between the microcantilever element and the substrate for a sufficient time as to allow hybridization or chemnical interaction to occur. Specifically, operation of the microcantilever detector apparatus is performed under fluid. The substrate made with different sample sites having samples attached to the surface, is placed under a buffer solution for hybridization or chemical/biochemical interactions to take place. Then, the microcantilever array is placed on top of the sample substrate array wherein the apparatus is still under fluid.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. An uncoated microcantilever detector apparatus comprising:
    a) at least a first microcantilever element being uncoated and comprising a material selected from the group consisting of electrically conductive materials and electrically semi-conductive materials;
    b) a substrate positioned adjacent said first microcantilever element and disposed relative to said first microcantilever element with a known, controlled gap therebetween, said substrate comprising a material selected from the group consisting of electrically conductive materials and electrically semi-conductive materials, said substrate further comprising means for attaching at least one sample upon said substrate proximate said first microcantilever element;
    c) a vibration detection means for detecting vibration of said first microcantilever element and providing vibration data;
    d) alternating voltage means disposed and connected for imposing an alternating voltage electrical signal to said substrate with respect to said first microcantilever element to induce vibration in said first microcantilever element;
    e) instrumentation means disposed and in communication with said first microcantilever element for receiving said vibration data and to determine frequency and amplitude of vibration of said first microcantilever element and for sensing and quantifying said alternating voltage electrical signal applied to said substrate with respect to said first microcantilever element; and further for detecting and quantifying differences in phase angle between said signal applied by said alternating voltage means and the signal generated by said vibration detection means; and
    f) said first microcantilever element, said substrate, said vibration detection means, said alternating voltage means, and said instrumentation means being configured to permit a test fluid to pass between said first microcantilever element and said substrate so that chemical interactions may occur between a component of said test fluid and a component of said sample.

2. The uncoated microcantilever detector apparatus of claim 1 wherein said first microcantilever element has at one light-reflecting surface and said vibration detection means comprises:
    a) a laser light source disposed and focused to project laser light onto said light-reflecting surface of said first microcantilever element; and,
    b) a position-sensitive photodetector disposed so that laser light reflected from said first microcantilever element is impinged upon the sensing element of said photodetector, said photodetector being configured and connected to provide vibration data to said instrumentation means.

3. The uncoated microcantilever detector apparatus of claim 1 wherein said first microcantilever element is an insulated piezoresistive microcantilever and said vibration detection means comprises:
    a) a Wheatstone bridge configured and connected to measure changes in microcantilever resistance; and
    b) an electrical circuit configured and connected to provide vibration data to said instrumentation means.

4. The uncoated microcantilever detector apparatus of claim 1 wherein said first microcantilever element is an insulated piezoelectric microcantilever and said vibration detection means comprises an electrical circuit configured and connected to measure the charge created due to vibration of said microcantilever element configured to provide vibration data to said instrumentation means.

5. The uncoated microcantilever detector apparatus of claim 1 wherein the detected signal is a phase angle difference between said signal applied to said substrate and the signal detected by said vibration detection means.

6. The uncoated microcantilever detector apparatus of claim 1 wherein the detected signal is the amplitude of vibration of said first microcantilever element.

7. The uncoated microcantilever detector apparatus of claim 1 wherein said substrate further comprises means for attaching a multiplicity of samples, and said first microcantilever element and said substrate are configured so that said first microcantilever element and any one of said samples is placed in appropriate proximity of each other in succession, pausing in appropriate proximity for sufficient time to determine the phase angle between the applied bias and that of vibration of said first microcantilever element.

8. The uncoated microcantilever detector apparatus of claim 7 further comprising recording means for comparing and recording parameters selected from the group consisting of differences in phase angle and differences in vibrational amplitude, identified by said sample positioned proximate to said first microcantilever element for identifying the chemical species of said sample.

9. The uncoated microcantilever detector apparatus of claim 7 comprises an array of microcantilever elements and said substrate is an array of sample elements positioned adjacent said array of microcantilever elements and disposed relative to said array of microcantilever elements with a known, controlled gap therebetween.

10. The uncoated microcantilever detector apparatus of claim 9 wherein said array of microcantilever elements further comprises a microcantilever readout means.

11. The uncoated microcantilever detector apparatus of claim 9 wherein said microcantilever elements of said array are insulated piezoresistive microcantilevers and said vibration detection means comprises:
    a) a Wheatstone bridge configured and connected to measure changes in microcantilever resistance; and
    b) an electrical circuit configured and connected to provide vibration data to said instrumentation means.

12. The uncoated microcantilever detector apparatus of claim 9 wherein said microcantilever elements of said array are insulated piezoelectric microcantilevers and said vibration detection means comprises an electrical circuit configured and connected to measure the charge created due to vibration of said microcantilever elements configured to provide vibration data to said instrumentation means.

13. The uncoated microcantilever detector apparatus of claim 7 wherein said substrate is configured in a linear pattern.

14. The uncoated microcantilever detector apparatus of claim 13 wherein said substrate is a continuous tape monitoring cassette.

15. The uncoated microcantilever detector apparatus of claim 7 wherein said substrate is configured as a disc wherein multiple samples are arranged in at least one pattern selected from the group consisting of arc patterns and circular patterns about the axis of rotation of said disc.

16. The uncoated microcantilever detector apparatus of claim 15 wherein said first microcantilever element is translated radially with respect to said disc in order to sense samples arranged in multiple patterns on said disc.

17. The uncoated microcantilever detector apparatus of claim 1 further comprising a proximity sensing means for sensing the distance between said first microcantilever element and said substrate.

18. The uncoated microcantilever detector apparatus of claim 17 wherein said proximity sensing means comprises a second microcantilever element brought into close proximity to said substrate by a proximity controlling means and said proximity sensing means connected to said second microcantilever element.

19. The uncoated microcantilever detector apparatus of claim 18 wherein said proximity controlling means comprises a piezoelectric transducer and a piezoelectric element, said piezoelectric transducer being electrically connected with said piezoelectric element and said piezoelectric element being fixedly attached to said second microcantilever element, said piezoelectric element being configured to bring said second microcantilever element into close proximity with said substrate and said second microcantilever element capable of being vibrated by activating said piezoelectric transducer, the amplitude of vibration of said second microcantilever element being a measure of proximity between said second microcantilever element and said substrate, and wherein the displacement of said second microcantilever element being a function of the voltage applied to said piezoelectric element.

20. The uncoated microcantilever detector apparatus of claim 19 wherein proximity of said second microcantilever element is indicated by amplitude of vibration of said second microcantilever element.

21. The uncoated microcantilever detector apparatus of claim 19 wherein proximity of said second microcantilever element to said substrate is indicated by deflection of said second microcantilever element due to contact between said second microcantilever element and said substrate.

22. The uncoated microcantilever detector apparatus of claim 1 wherein the response of said first microcantilever element is monitored at the frequency of said applied alternating voltage applied to said substrate or at the harmonics of said applied alternating voltage on said substrate.

23. A method for detecting a component capable of chemical interaction or hybridization in a fluid test sample comprising the steps of:
  a) providing an uncoated microcantilever detector apparatus comprising at least one microcantilever element, said microcantilever element being uncoated and comprising a material selected from the group consisting of electrically conductive materials and electrically semi-conductive materials, also comprising a substrate positioned adjacent said microcantilever element and disposed relative to said microcantilever element with a known, controlled gap therebetween, said substrate comprising a material selected from the group consisting of electrically conductive materials and electrically semi-conductive materials, said substrate further comprising means for attaching at least one sample upon said substrate proximate said microcantilever element, further comprising a vibration detection means for detecting vibration of said microcantilever element and providing vibration data, an alternating voltage means disposed and connected for imposing an alternating voltage electrical signal to said substrate with respect to said mitrocantilever element to induce vibration in said microcantilever element, an instrumentation means disposed and connected for receiving said vibration data and to determine frequency and amplitude of vibration of said microcantilever element and for sensing and quantifying said alternating voltage electrical signal applied to said substrate with respect to said microcantilever element, and also for detecting and quantifying differences in phase angle between the signal applied by said alternating voltage means and the signal generated by said vibration detection means, said microcantilever element, said substrate, said vibration detection means, said alternating voltage means, and said instrumentation means being configured to permit a test fluid to pass between said microcantilever element and said; substrate so that said chemical interaction or said hybridization may occur between a component of said test fluid and a component of said sample;
  b) causing said test fluid to pass between said microcantilever element and said substrate to allow for said chemical interaction or said hybridization to occur; and
  c) determining the frequency and amplitude of vibration of said microcantilever element and quantifying differences in phase angle between said alternating voltage electrical signal applied by said alternating voltage means and the signal generated by said vibration detection means so to determine whether said chemical interaction or said hybridization occurred and so to determine the extent of chemical interaction or hybridization which may have occurred between said component of said test fluid and said component of said sample.

24. The method of claim 23 wherein said microcantilever element has at one light-reflecting surface and said vibration detection means comprises:
  a) a laser light source disposed and focused to project laser light onto said light-reflecting surface of said microcantilever element; and
  b) a position-sensitive photodetector disposed so that laser light reflected from said microcantilever element is impinged upon the sensing element of said photodetector, said photodetector being configured and connected to provide vibration data to said instrumentation means.

25. The method of claim 23 wherein said microcantilever element is an insulated piezoresistive microcantilever and said vibration detection means comprises:
  a) a Wheatstone bridge configured and connected to measure changes in microcantilever resistance; and
  b) an electrical circuit configured and connected to provide vibration data to said instrumentation means.

26. The method of claim 23 wherein said microcantilever element is an insulated piezoelectric microcantilever and said vibration detection means comprises an electrical circuit configured and connected to measure the charge created due to vibration of said microcantilever element configured to provide vibration data to said instrumentation means.

27. The method of claim 23 wherein the detected signal is a phase angle difference between said signal applied to said substrate and the signal detected by said vibration detection means.

28. The method of claim 23 wherein the detected signal is the amplitude of vibration of said uncoated microcantilever element.

29. The method of claim 23 wherein said substrate further comprises means for attaching a multiplicity of samples, and said microcantilever element and said substrate are configured so that said microcantilever element and any one of said samples is placed in appropriate proximity of each other in succession, pausing in appropriate proximity for sufficient time to determine the phase angle between the applied bias and that of vibration of said microcantilever element.

30. The method of claim 29 wherein said apparatus further comprises recording means for comparing and recording parameters selected from the group consisting of differences in phase angle and differences in vibrational amplitude, identified by said sample positioned proximate to said microcantilever element for identifying the component of said sample.

31. The method of claim 29 wherein said apparatus further comprises an array of microcantilever elements and said substrate is an array of sample elements positioned adjacent said array of microcantilever elements and disposed relative to said array of microcantilever elements with a known, controlled gap therebetween.

32. The method of claim 31 wherein said array of microcantilever elements further comprises a microcantilever readout means.

33. The method of claim 29 wherein said substrate is configured as a disc wherein multiple samples are arranged in at least one pattern selected from the group consisting of arc patterns and circular patterns about the axis of rotation of said disc.

34. The method of claim 29 wherein said substrate is configured in a linear pattern.

35. The method of claim 34 wherein said substrate is a continuous tape monitoring cassette.

36. The method of claim 23 wherein said apparatus further comprises a proximity sensing means for sensing the distance between said microcantilever element and said substrate.

37. The method of claim 36 wherein said proximity sensing means comprises a second microcantilever element brought into close proximity to said substrate by a proximity controlling means and said proximity sensing means connected to said second microcantilever element.

38. The method of claim 37 wherein said proximity controlling means comprises a piezoelectric transducer and a piezoelectric element, said piezoelectric transducer being electrically connected with said piezoelectric element and said piezoelectric element being fixedly attached to said second microcantilever element, said piezoelectric element being configured to bring said second microcantilever element into close proximity with said substrate and said second microcantilever element capable of being vibrated by activating said piezoelectric transducer, the amplitude of vibration of said second microcantilever element being a measure of proximity between said second microcantilever element and said substrate, and wherein the displacement of said second microcantilever element being a function of the voltage applied to said piezoelectric element.

39. The method of claim 38 wherein proximity of said second microcantilever element is indicated by amplitude of vibration of said second microcantilever element.

40. The method of claim 38 wherein proximity of said second microcantilever element to said substrate is indicated by deflection of said second microcantilever element due to contact between said second microcantilever element and said substrate.

41. The method of claim 23 wherein the response of said microcantilever element is monitored at the frequency of said applied alternating voltage applied to said substrate or at the harmonics of said applied alternating voltage on said substrate.

* * * * *